(12) United States Patent
Ritland (10) Patent No.: US 7,959,564 B2
(45) Date of Patent: Jun. 14, 2011

(54) PEDICLE SEEKER AND RETRACTOR, AND METHODS OF USE

(76) Inventor: Stephen Ritland, Flagstaff, AZ (US)

( * ) Notice: Subject to any disclaimer, the term of this patent is extended or adjusted under 35 U.S.C. 154(b) by 444 days.

(21) Appl. No.: 11/774,806

(22) Filed: Jul. 9, 2007

(65) Prior Publication Data

US 2008/0009678 A1 Jan. 10, 2008

Related U.S. Application Data

(60) Provisional application No. 60/806,775, filed on Jul. 8, 2006.

(51) Int. Cl.
*A61B 17/88* (2006.01)
(52) U.S. Cl. .................. 600/201; 606/279; 606/86 A
(58) Field of Classification Search .................. 606/104, 606/201, 88, 73, 300, 86 A, 96–99, 279; 600/201, 600/207, 210
See application file for complete search history.

(56) References Cited

U.S. PATENT DOCUMENTS

| | | | |
|---|---|---|---|
| 2,191 | A | 7/1841 | Pitney |
| 569,839 | A | 10/1896 | Roeloffs |
| 605,652 | A | 6/1898 | Pitt |
| 1,090,746 | A | 3/1914 | Nourse |
| 1,097,978 | A | 5/1914 | Johnson |
| 3,467,079 | A | 9/1969 | James |
| 3,470,872 | A | 10/1969 | Grieshaber |
| 3,875,595 | A | 4/1975 | Froning |
| 3,893,454 | A | 7/1975 | Hagelin |

(Continued)

FOREIGN PATENT DOCUMENTS

EP 0820731 1/1998

(Continued)

OTHER PUBLICATIONS

International Preliminary Examination Report issued Mar. 23, 2004, in related Application PCT/US2002/002703.

(Continued)

*Primary Examiner* — Eduardo C Robert
*Assistant Examiner* — Christian Sevilla
(74) *Attorney, Agent, or Firm* — Holme Roberts & Owen LLP (57) ABSTRACT

To avoid traditional muscle dissection required in the placement of a surgical implant during arthrodesis, a pedicle seeker and retractor are provided. The pedicle seeker includes a distal end that approximates the size, shape and length of a surgical implant and is of sufficient length to extend beyond the face of the retractor, allowing the pedicle seeker to be removed from the surgical site once the retractor has been placed. The pedicle seeker is used to palpate the bony surface of the patient's spine in order to locate the proper place to place an implant. After the desired location has been located, the retractor is placed into the surgical site and held in place in order to maintain the desired location for placement of the surgical implant, and the seeker is removed. The retractor includes surficial features that approximate the size of the pedicle seeker and the surgical implant, to allow the implant to be moved down the length of the face of the retractor to the desired location. The retractor therefore provides a guide for the desired implant to be to the desired location and is configured to retract as the implant is advanced into position. The pedicle seeker and retractor of the present invention thus allow for accurate, protected placement of a surgical implant without the use of a retractor insert, or similar article.

7 Claims, 4 Drawing Sheets

U.S. PATENT DOCUMENTS

| | | | |
|---|---|---|---|
| 4,041,939 A | 8/1977 | Hall | |
| 4,232,660 A | 11/1980 | Coles | |
| 4,437,458 A * | 3/1984 | Upsher | 600/193 |
| 4,440,168 A | 4/1984 | Warren | |
| 4,481,947 A | 11/1984 | Chester | |
| 4,545,374 A | 10/1985 | Jacobson | |
| 4,573,448 A | 3/1986 | Kambin | |
| 4,617,922 A | 10/1986 | Griggs | |
| 4,620,460 A | 11/1986 | Gonzales, Jr. | |
| 4,686,972 A * | 8/1987 | Kurland | 606/96 |
| 4,736,738 A | 4/1988 | Lipovsek | |
| 4,743,260 A | 5/1988 | Burton | |
| 4,747,394 A | 5/1988 | Watanabe | |
| 4,798,111 A | 1/1989 | Cheeseman | |
| 4,803,976 A | 2/1989 | Frigg | |
| 4,817,587 A | 4/1989 | Janese | |
| 4,862,891 A | 9/1989 | Smith | |
| 4,863,423 A | 9/1989 | Wallace | |
| 4,882,958 A | 11/1989 | McNeeley | |
| 4,889,112 A | 12/1989 | Schachner et al. | |
| 4,974,985 A | 12/1990 | Glatzel | |
| 4,995,875 A | 2/1991 | Coes | |
| 5,002,542 A | 3/1991 | Frigg | |
| 5,002,576 A | 3/1991 | Fuhrmann et al. | |
| 5,018,507 A | 5/1991 | Montaldi | |
| 5,026,373 A | 6/1991 | Ray et al. | |
| 5,030,220 A | 7/1991 | Howland | |
| 5,030,223 A | 7/1991 | Anderson et al. | |
| 5,035,232 A | 7/1991 | Lutze et al. | |
| 5,048,379 A | 9/1991 | Gramera | |
| 5,052,373 A | 10/1991 | Michelson | |
| 5,055,104 A | 10/1991 | Ray | |
| 5,084,043 A | 1/1992 | Hertzmann | |
| 5,098,435 A | 3/1992 | Stednitz | |
| 5,106,376 A | 4/1992 | Mononen | |
| 5,129,900 A | 7/1992 | Asher et al. | |
| 5,133,720 A | 7/1992 | Greenberg | |
| 5,135,525 A | 8/1992 | Biscoping | |
| 5,148,724 A | 9/1992 | Rexford | |
| 5,158,543 A | 10/1992 | Lazarus | |
| 5,165,306 A | 11/1992 | Hellon | |
| 5,195,541 A | 3/1993 | Obenchain | |
| 5,217,007 A | 6/1993 | Ciaglia | |
| 5,275,600 A | 1/1994 | Allard et al. | |
| 5,275,611 A * | 1/1994 | Behl | 606/198 |
| 5,279,567 A | 1/1994 | Ciaglia | |
| 5,292,309 A | 3/1994 | Van Tassel | |
| 5,303,694 A | 4/1994 | Mikhail | |
| 5,306,275 A | 4/1994 | Bryan | |
| 5,306,309 A | 4/1994 | Wagner et al. | |
| 5,312,360 A | 5/1994 | Behl | |
| 5,312,405 A | 5/1994 | Korotko et al. | |
| 5,330,474 A | 7/1994 | Lin | |
| 5,334,194 A * | 8/1994 | Mikhail | 606/88 |
| 5,356,413 A | 10/1994 | Martins et al. | |
| 5,363,841 A | 11/1994 | Coker | |
| 5,397,330 A * | 3/1995 | Mikhail | 606/88 |
| 5,415,661 A | 5/1995 | Holmes | |
| 5,431,639 A | 7/1995 | Shaw | |
| 5,431,651 A | 7/1995 | Goble | |
| D361,381 S | 8/1995 | Koros et al. | |
| 5,439,464 A | 8/1995 | Shapiro | |
| 5,466,238 A | 11/1995 | Lin | |
| 5,472,426 A | 12/1995 | Bonati | |
| 5,474,555 A | 12/1995 | Puno et al. | |
| 5,484,440 A | 1/1996 | Allard | |
| 5,489,274 A | 2/1996 | Chu | |
| 5,489,308 A | 2/1996 | Kuslich et al. | |
| 5,498,262 A | 3/1996 | Bryan | |
| 5,499,983 A | 3/1996 | Hughes | |
| 5,501,684 A | 3/1996 | Schlapfer et al. | |
| 5,512,038 A | 4/1996 | O'Neal et al. | |
| 5,558,622 A | 9/1996 | Greenberg | |
| 5,565,502 A | 10/1996 | Glimcher et al. | |
| 5,569,300 A | 10/1996 | Redmon | |
| 5,584,833 A | 12/1996 | Fournet-Fayard et al. | |
| 5,591,166 A | 1/1997 | Bernhardt et al. | |
| 5,591,235 A | 1/1997 | Kuslich | |
| 5,593,409 A | 1/1997 | Michelson | |
| 5,601,550 A | 2/1997 | Esser | |
| 5,603,714 A | 2/1997 | Kaneda et al. | |
| 5,611,778 A | 3/1997 | Brinon | |
| 5,628,740 A | 5/1997 | Mullane | |
| 5,643,263 A | 7/1997 | Simonson | |
| 5,643,264 A | 7/1997 | Sherman et al. | |
| 5,645,544 A | 7/1997 | Tai et al. | |
| 5,645,599 A | 7/1997 | Samani | |
| 5,683,392 A | 11/1997 | Richelsoph et al. | |
| 5,683,463 A | 11/1997 | Godefroy et al. | |
| 5,687,739 A | 11/1997 | McPherson | |
| 5,690,632 A | 11/1997 | Schwartz et al. | |
| 5,691,397 A | 11/1997 | Glimcher et al. | |
| 5,702,455 A | 12/1997 | Saggar | |
| 5,716,355 A | 2/1998 | Jackson et al. | |
| 5,716,415 A | 2/1998 | Steffee | |
| 5,725,528 A | 3/1998 | Errico et al. | |
| 5,735,850 A | 4/1998 | Baumgartner et al. | |
| 5,735,851 A | 4/1998 | Errico et al. | |
| 5,735,899 A | 4/1998 | Schwartz et al. | |
| 5,743,853 A | 4/1998 | Lauderdale | |
| 5,746,720 A | 5/1998 | Stouder, Jr. | |
| 5,746,741 A | 5/1998 | Kraus et al. | |
| 5,752,957 A | 5/1998 | Ralph et al. | |
| 5,766,221 A | 6/1998 | Benderev et al. | |
| 5,766,253 A | 6/1998 | Brosnahan, III | |
| 5,772,582 A | 6/1998 | Huttner et al. | |
| 5,782,832 A | 7/1998 | Larsen et al. | |
| 5,785,648 A | 7/1998 | Min | |
| 5,785,710 A | 7/1998 | Michelson | |
| 5,785,712 A | 7/1998 | Runciman et al. | |
| 5,792,044 A | 8/1998 | Foley | |
| 5,797,912 A | 8/1998 | Runciman et al. | |
| 5,800,435 A | 9/1998 | Errico et al. | |
| 5,810,816 A | 9/1998 | Roussouly et al. | |
| 5,810,817 A | 9/1998 | Roussouly et al. | |
| D399,955 S | 10/1998 | Koros et al. | |
| 5,816,257 A | 10/1998 | Chin | |
| 5,827,328 A | 10/1998 | Buttermann | |
| 5,836,948 A | 11/1998 | Zucherman et al. | |
| RE36,020 E | 12/1998 | Moore et al. | |
| 5,851,207 A * | 12/1998 | Cesarone | 606/86 B |
| 5,860,977 A | 1/1999 | Zucherman et al. | |
| 5,865,847 A | 2/1999 | Kohrs et al. | |
| 5,865,848 A | 2/1999 | Baker | |
| 5,876,404 A | 3/1999 | Zucherman et al. | |
| 5,882,344 A | 3/1999 | Stouder, Jr. | |
| 5,885,285 A | 3/1999 | Simonson | |
| 5,885,299 A | 3/1999 | Winslow et al. | |
| 5,885,300 A | 3/1999 | Tokuhashi et al. | |
| 5,891,147 A | 4/1999 | Moskovitz et al. | |
| 5,895,352 A | 4/1999 | Kleiner | |
| 5,895,390 A | 4/1999 | Moran et al. | |
| 5,897,593 A | 4/1999 | Kohrs et al. | |
| 5,899,901 A | 5/1999 | Middleton | |
| 5,902,231 A | 5/1999 | Foley | |
| 5,902,304 A | 5/1999 | Walker | |
| 5,904,650 A | 5/1999 | Wells | |
| 5,906,616 A | 5/1999 | Pavlov et al. | |
| 5,913,818 A | 6/1999 | Co et al. | |
| 5,928,139 A | 7/1999 | Koros | |
| 5,928,233 A | 7/1999 | Apfelbaum et al. | |
| 5,938,663 A | 8/1999 | Petreto | |
| 5,944,658 A | 8/1999 | Koros et al. | |
| 5,947,965 A | 9/1999 | Bryan | |
| 5,954,635 A | 9/1999 | Foley | |
| 5,954,671 A | 9/1999 | O'Neill | |
| 5,961,516 A | 10/1999 | Graf | |
| 5,967,970 A | 10/1999 | Cowan | |
| 5,968,098 A | 10/1999 | Winslow | |
| 5,971,920 A | 10/1999 | Nagel | |
| 5,976,135 A | 11/1999 | Sherman et al. | |
| 5,976,146 A | 11/1999 | Ogawa | |
| 5,984,924 A | 11/1999 | Asher et al. | |
| 5,996,447 A | 12/1999 | Bayouth | |
| 5,997,539 A | 12/1999 | Errico et al. | |
| 6,004,322 A | 12/1999 | Bernstein | |
| 6,007,487 A | 12/1999 | Foley et al. | |

| Patent No. | Kind | Date | Inventor |
|---|---|---|---|
| 6,010,520 | A | 1/2000 | Pattison |
| 6,017,342 | A | 1/2000 | Rinner |
| 6,027,533 | A | 2/2000 | Olerud |
| 6,045,579 | A | 4/2000 | Hochshuler et al. |
| 6,048,342 | A | 4/2000 | Zucherman et al. |
| 6,050,997 | A | 4/2000 | Mullane |
| 6,063,088 | A | 5/2000 | Winslow |
| 6,068,630 | A | 5/2000 | Zucherman et al. |
| 6,074,390 | A | 6/2000 | Zucherman et al. |
| 6,074,393 | A | 6/2000 | Sitoto |
| 6,080,155 | A | 6/2000 | Michelson |
| 6,080,193 | A | 6/2000 | Hochshuler et al. |
| 6,081,741 | A | 6/2000 | Hollis |
| 6,083,225 | A | 7/2000 | Winslow et al. |
| 6,090,112 | A | 7/2000 | Zucherman et al. |
| 6,102,948 | A | 8/2000 | Brosnahan, III |
| 6,113,602 | A | 9/2000 | Sand |
| 6,117,137 | A | 9/2000 | Halm et al. |
| 6,117,174 | A | 9/2000 | Nolan |
| 6,120,434 | A | 9/2000 | Kimura |
| 6,120,506 | A | 9/2000 | Kohrs et al. |
| 6,123,705 | A | 9/2000 | Michelson |
| 6,123,706 | A | 9/2000 | Lange |
| 6,132,430 | A | 10/2000 | Wagner |
| D433,296 | S | 11/2000 | Yamakawa |
| 6,146,383 | A | 11/2000 | Studer et al. |
| 6,149,652 | A | 11/2000 | Zucherman et al. |
| 6,149,686 | A | 11/2000 | Kuslich et al. |
| 6,152,871 | A | 11/2000 | Foley |
| 6,152,926 | A | 11/2000 | Zucherman et al. |
| 6,156,006 | A | 12/2000 | Brosens |
| 6,156,038 | A | 12/2000 | Zucherman et al. |
| 6,159,179 | A | 12/2000 | Simonson |
| 6,162,170 | A | 12/2000 | Foley |
| 6,162,236 | A | 12/2000 | Osada |
| D436,513 | S | 1/2001 | Yamakawa |
| 6,176,823 | B1 | 1/2001 | Foley |
| 6,176,861 | B1 | 1/2001 | Bernstein et al. |
| 6,179,838 | B1 | 1/2001 | Fiz |
| D438,074 | S | 2/2001 | Marr |
| 6,183,471 | B1 | 2/2001 | Zucherman et al. |
| 6,187,005 | B1 | 2/2001 | Brace et al. |
| 6,190,387 | B1 | 2/2001 | Zucherman et al. |
| 6,190,414 | B1 | 2/2001 | Young et al. |
| 6,196,696 | B1 | 3/2001 | Shiao |
| 6,196,969 | B1 | 3/2001 | Bester et al. |
| 6,197,002 | B1 | 3/2001 | Peterson |
| 6,206,822 | B1 | 3/2001 | Foley |
| 6,206,826 | B1 | 3/2001 | Mathews et al. |
| 6,206,885 | B1 | 3/2001 | Ghahremani et al. |
| 6,206,922 | B1 | 3/2001 | Zdeblick et al. |
| 6,206,923 | B1 | 3/2001 | Boyd et al. |
| 6,210,413 | B1 | 4/2001 | Justis et al. |
| 6,214,004 | B1 | 4/2001 | Coker |
| 6,217,509 | B1 | 4/2001 | Foley |
| 6,224,597 | B1 | 5/2001 | Coker |
| 6,224,608 | B1 | 5/2001 | Ciccolella |
| 6,224,631 | B1 | 5/2001 | Kohrs |
| 6,231,575 | B1 | 5/2001 | Krag |
| 6,235,030 | B1 | 5/2001 | Zucherman et al. |
| 6,238,397 | B1 | 5/2001 | Zucherman et al. |
| 6,245,072 | B1 | 6/2001 | Zdeblick et al. |
| 6,248,104 | B1 | 6/2001 | Chopin et al. |
| 6,248,106 | B1 | 6/2001 | Ferree |
| 6,258,097 | B1 | 7/2001 | Cook |
| 6,261,287 | B1 | 7/2001 | Metz-Stavenhagen |
| 6,264,658 | B1 | 7/2001 | Lee et al. |
| 6,267,763 | B1 | 7/2001 | Castro |
| 6,267,764 | B1 | 7/2001 | Elberg |
| 6,267,765 | B1 | 7/2001 | Taylor et al. |
| 6,270,498 | B1 | 8/2001 | Michelson |
| 6,273,914 | B1 | 8/2001 | Papas |
| 6,283,966 | B1 | 9/2001 | Houfburg |
| 6,287,309 | B1 | 9/2001 | Baccelli et al. |
| 6,287,313 | B1 | 9/2001 | Sasso |
| 6,287,343 | B1 | 9/2001 | Kuslich et al. |
| 6,290,700 | B1 | 9/2001 | Schmotzer |
| 6,293,949 | B1 | 9/2001 | Justis et al. |
| 6,296,609 | B1 | 10/2001 | Brau |
| 6,299,614 | B1 | 10/2001 | Kretschmer et al. |
| 6,302,842 | B1 | 10/2001 | Auerbach et al. |
| 6,309,390 | B1 | 10/2001 | Le Couedic et al. |
| 6,309,391 | B1 | 10/2001 | Crandall et al. |
| 6,312,432 | B1 | 11/2001 | Leppelmeier |
| 6,332,883 | B1 | 12/2001 | Zucherman et al. |
| 6,342,056 | B1 * | 1/2002 | Mac-Thiong et al. .......... 606/96 |
| 6,342,057 | B1 | 1/2002 | Brace |
| 6,348,058 | B1 | 2/2002 | Melkent et al. |
| 6,354,176 | B1 | 3/2002 | Nordlin |
| 6,355,038 | B1 | 3/2002 | Pisharodi |
| 6,361,541 | B1 | 3/2002 | Barnhart |
| 6,368,350 | B1 | 4/2002 | Erickson et al. |
| 6,368,351 | B1 | 4/2002 | Glenn et al. |
| 6,371,959 | B1 | 4/2002 | Trice |
| 6,371,968 | B1 | 4/2002 | Kogasaka |
| 6,391,058 | B1 | 5/2002 | Kuslich et al. |
| 6,395,033 | B1 | 5/2002 | Pepper |
| 6,418,821 | B1 | 7/2002 | Yamakawa |
| 6,425,901 | B1 | 7/2002 | Zhu et al. |
| 6,428,472 | B1 | 8/2002 | Haas |
| 6,440,169 | B1 | 8/2002 | Elberg et al. |
| 6,440,170 | B1 | 8/2002 | Jackson |
| 6,443,953 | B1 | 9/2002 | Perra et al. |
| 6,443,989 | B1 | 9/2002 | Jackson |
| 6,461,330 | B1 | 10/2002 | Miyagi |
| 6,461,359 | B1 | 10/2002 | Tribus et al. |
| 6,471,724 | B2 | 10/2002 | Zdeblick et al. |
| 6,478,798 | B1 | 11/2002 | Howland |
| D466,766 | S | 12/2002 | Marty |
| 6,506,151 | B2 | 1/2003 | Estes |
| 6,520,907 | B1 | 2/2003 | Foley |
| 6,524,238 | B2 | 2/2003 | Velikaris et al. |
| 6,530,880 | B2 | 3/2003 | Pagliuca |
| 6,530,926 | B1 | 3/2003 | Davison |
| 6,540,756 | B1 | 4/2003 | Vaughan |
| 6,551,320 | B2 | 4/2003 | Lieberman |
| 6,554,831 | B1 | 4/2003 | Rivard et al. |
| 6,562,046 | B2 | 5/2003 | Sasso |
| 6,562,073 | B2 | 5/2003 | Foley |
| 6,565,569 | B1 | 5/2003 | Assaker et al. |
| 6,569,164 | B1 | 5/2003 | Assaker et al. |
| 6,576,017 | B2 | 6/2003 | Foley et al. |
| 6,579,292 | B2 | 6/2003 | Taylor |
| 6,585,738 | B1 | 7/2003 | Mangione et al. |
| 6,595,993 | B2 | 7/2003 | Donno et al. |
| 6,610,062 | B2 | 8/2003 | Bailey et al. |
| 6,626,904 | B1 | 9/2003 | Jammet et al. |
| 6,626,906 | B1 | 9/2003 | Young |
| 6,648,887 | B2 | 11/2003 | Ashman |
| 6,671,725 | B1 | 12/2003 | Noel, Jr. et al. |
| 6,676,661 | B1 | 1/2004 | Martin Benlloch et al. |
| 6,679,833 | B2 | 1/2004 | Smith |
| 6,682,532 | B2 | 1/2004 | Johnson et al. |
| 6,685,705 | B1 | 2/2004 | Taylor |
| 6,692,434 | B2 | 2/2004 | Ritland |
| 6,736,816 | B2 | 5/2004 | Ritland |
| 6,743,257 | B2 | 6/2004 | Castro |
| 6,749,613 | B1 | 6/2004 | Conchy et al. |
| 6,749,614 | B2 | 6/2004 | Teitelbaum et al. |
| 6,752,832 | B2 | 6/2004 | Neumann |
| 6,761,719 | B2 | 7/2004 | Justis et al. |
| 6,783,528 | B2 | 8/2004 | Vincent-Prestigiacomo |
| 6,851,430 | B2 | 2/2005 | Tsou |
| 6,916,319 | B2 | 7/2005 | Munting |
| 6,916,330 | B2 | 7/2005 | Simonson |
| 6,929,606 | B2 | 8/2005 | Ritland |
| 6,951,538 | B2 | 10/2005 | Ritland |
| 6,955,678 | B2 | 10/2005 | Gabriel et al. |
| 6,966,910 | B2 | 11/2005 | Ritland |
| 6,974,480 | B2 | 12/2005 | Messerli et al. |
| 6,991,632 | B2 | 1/2006 | Ritland |
| 7,008,431 | B2 | 3/2006 | Simonson |
| 7,166,073 | B2 | 1/2007 | Ritland |
| 7,207,992 | B2 | 4/2007 | Ritland |
| 7,214,186 | B2 | 5/2007 | Ritland |
| 2001/0005796 | A1 | 6/2001 | Zdeblick et al. |
| 2001/0010021 | A1 | 7/2001 | Boyd et al. |
| 2001/0012942 | A1 | 8/2001 | Estes |

| | | |
|---|---|---|
| 2001/0027320 A1 | 10/2001 | Sasso |
| 2001/0047207 A1 | 11/2001 | Michelson |
| 2002/0011135 A1 | 1/2002 | Hall |
| 2002/0016592 A1 | 2/2002 | Branch |
| 2002/0022764 A1 | 2/2002 | Smith |
| 2002/0029082 A1 | 3/2002 | Muhanna |
| 2002/0045904 A1* | 4/2002 | Fuss et al. ............... 606/99 |
| 2002/0049368 A1 | 4/2002 | Ritland |
| 2002/0058948 A1 | 5/2002 | Arlettaz |
| 2002/0068973 A1 | 6/2002 | Jackson |
| 2002/0068975 A1 | 6/2002 | Teitelbaum et al. |
| 2002/0077632 A1 | 6/2002 | Tsou |
| 2002/0082695 A1 | 6/2002 | Neumann |
| 2002/0107571 A1 | 8/2002 | Foley |
| 2002/0107572 A1 | 8/2002 | Foley et al. |
| 2002/0120270 A1 | 8/2002 | Trieu et al. |
| 2002/0123668 A1 | 9/2002 | Ritland |
| 2002/0143235 A1 | 10/2002 | Pagliuca |
| 2003/0083688 A1 | 5/2003 | Simonson |
| 2003/0083689 A1 | 5/2003 | Simonson |
| 2003/0093078 A1 | 5/2003 | Ritland |
| 2003/0109880 A1 | 6/2003 | Shirado et al. |
| 2003/0139812 A1 | 7/2003 | Garcia et al. |
| 2003/0144665 A1 | 7/2003 | Munting |
| 2003/0171749 A1 | 9/2003 | Le Couedic et al. |
| 2003/0171751 A1 | 9/2003 | Ritland |
| 2003/0187431 A1 | 10/2003 | Simonson |
| 2003/0191470 A1 | 10/2003 | Ritland |
| 2003/0220689 A1 | 11/2003 | Ritland |
| 2003/0225364 A1* | 12/2003 | Kraft et al. ............... 604/35 |
| 2003/0236447 A1* | 12/2003 | Ritland ............... 600/210 |
| 2004/0002708 A1 | 1/2004 | Ritland |
| 2004/0073229 A1* | 4/2004 | Yang ............... 606/104 |
| 2004/0106997 A1 | 6/2004 | Lieberson |
| 2004/0138534 A1 | 7/2004 | Ritland |
| 2004/0172023 A1 | 9/2004 | Ritland |
| 2004/0181223 A1 | 9/2004 | Ritland |
| 2004/0254428 A1 | 12/2004 | Ritland |
| 2005/0004593 A1* | 1/2005 | Simonson ............... 606/191 |
| 2005/0020920 A1 | 1/2005 | Ritland |
| 2005/0027360 A1 | 2/2005 | Webb et al. |
| 2005/0143737 A1 | 6/2005 | Paffard et al. |
| 2005/0149023 A1 | 7/2005 | Ritland |
| 2005/0149191 A1 | 7/2005 | Cragg et al. |
| 2005/0192575 A1* | 9/2005 | Pacheco ............... 606/61 |
| 2005/0203517 A1 | 9/2005 | Jahng et al. |
| 2005/0203519 A1 | 9/2005 | Harms et al. |
| 2005/0209694 A1 | 9/2005 | Loeb |
| 2005/0228233 A1 | 10/2005 | Ritland |
| 2006/0009768 A1 | 1/2006 | Ritland |
| 2006/0041259 A1 | 2/2006 | Paul et al. |
| 2006/0064090 A1 | 3/2006 | Park |
| 2006/0069390 A1 | 3/2006 | Frigg et al. |
| 2006/0079899 A1 | 4/2006 | Ritland |
| 2007/0016193 A1 | 1/2007 | Ritland |
| 2008/0132904 A1* | 6/2008 | Usher et al. ............... 606/104 |

FOREIGN PATENT DOCUMENTS

| | | |
|---|---|---|
| FR | 2796828 | 2/2001 |
| WO | WO 99/40866 | 8/1999 |
| WO | WO 00/18306 | 4/2000 |
| WO | WO 02/02022 | 1/2002 |
| WO | WO 02/07621 | 1/2002 |
| WO | WO 02/060330 | 8/2002 |
| WO | WO 03/026523 | 4/2003 |
| WO | WO 03/073908 | 9/2003 |
| WO | WO 03/094699 | 11/2003 |
| WO | WO 2004/075778 | 9/2004 |
| WO | WO 2004/089244 | 10/2004 |

OTHER PUBLICATIONS

International Search Report issued Jul. 1, 2002, in related Application PCT/US2002/002703.
Final Office Action dated Jun. 25, 2009, in related U.S. Appl. No. 10/853,623.
Response to Office Action filed Jan. 21, 2009, in related U.S. Appl. No. 10/853,623.
Office Action dated Oct. 17, 2008, in related U.S. Appl. No. 10/853,623.
Response to Office Action filed Jul. 3, 2008, in related U.S. Appl. No. 10/853,623.
Office Action dated Jul. 25, 2007, in related U.S. Appl. No. 10/853,623.
Response to Office Action filed Oct. 2, 2006, in related U.S. Appl. No. 10/853,623.
Office Action dated Jun. 1, 2006, in related U.S. Appl. No. 10/853,623.
Response to Office Action filed May 4, 2006, in related U.S. Appl. No. 10/853,623.
Final Office Action dated Mar. 9, 2006, in related U.S. Appl. No. 10/853,623.
Response to Office Action filed Dec. 8, 2005, in related U.S. Appl. No. 10/853,623.
Office Action dated Sep. 8, 2005, in related U.S. Appl. No. 10/853,623.
Office Action dated Oct. 30, 2007, in related U.S. Appl. No. 11/228,106.
Response to Office Action filed Mar. 31, 2008, in related U.S. Appl. No. 11/228,106.
Final Office Action dated Jul. 9, 2008, in related U.S. Appl. No. 11/228,106.
Response to Office Action filed Aug. 12, 2008, in related U.S. Appl. No. 11/228,106.
Notice of Allowance dated Oct. 1, 2008 in related U.S. Appl. No. 11/228,106.
International Preliminary Report on Patentability issued Dec. 8, 2005, in related Application PCT/US2004/016446.
Written Opinion issued Oct. 18, 2005, in related Application PCT/US2004/016446.
International Search Report issued Oct. 18, 2005, in related Application PCT/US2004/016446.
Hilton et al.; "Meditronic Sofamor Danek METRIX Microdiscectomy: Minimal Intervention in Spinal Surgery"; National Library of Medicine; 1991; 67-100.
Response to Office Action filed Nov. 26, 2007 in related U.S. Appl. No. 10/853,623.
U.S. Appl. No. 10/165,991, filed Jun. 10, 2002, Simonson.
"New Minimally Invasive Techniques, Improve Outcome of Spine Surgeries", Medtronic Sofamor Danek. Date unknown, 1 page.
Caspar; "Technique of Microsurgery: Microsurgery of the Lumbar Spine: Principles and Techniques in Spine Surgery"; Aspen Publications; 1990; 105-122.
China Chemical Reporter, "Rapid Development of Polyether Ether Ketone", CNCIC Chemdata Inc., 2004, 2 pages.
Green, "Body Building—Medical Materials for Systems and Scaffolding," Materials World, Journal of the Institute of Materials, vol. 10, No. 2, 2001, 4 pages.
Green, "Effects of Gamma Sterilisation on Implant Grade Polyetheretherketone," Invibio Inc., Lancashire, United Kingdom, undated, 1 page.
Green, "In Vivo Biostability Study on Polyaryletheretherketone Biomaterial," Invibio Inc., Lancashire, United Kingdom, undated, 2 pages.
Green, et al., "A Polyaryletherketone Biomaterial for Use in Medical Implant Applications," Lancashire, United Kingdom, 2001, 1 page.
Green, et al., "Polyetheretherketone Polymer and Compounds for Surgical Applications," Lancashire, United Kingdom, undated, 9 pages.
Green, Stuart, "PEEK-Optima Polymer in the Implantable Medical Device Industry," Invibio Inc., Lancashire, United Kingdom, undated, 2 pages.
Invibio, Biomaterials Solutions, "High Performance PEEK-Optima Biocompatible Polymer Chosen for Dental Abutment Healing Caps," Invibio Inc., Lancashire, United Kingdom, undated, 1 page.
Invibio, Biomaterials Solutions, "High Performance PEEK-Optima Biocompatible Polymer Chosen for New Generation Heart Valve," Invibio Inc., Lancashire, United Kingdom, undated, 1 page.
Invibio, Biomaterials Solutions, "PEEK-Classix," Invibio Inc., Lancashire, United Kingdom, 2003, 2 pages.

Invibio, Biomaterials Solutions, "PEEK-Optima Polymer: Performance Purity Flexibility Endurance," Invibio Inc., Lancashire, United Kingdom, 2004, 3 pages.

Invibio, Biomaterials Solutions, "PEEK-Optima, Composite Hip," Invibio Inc., Lancashire, United Kingdom, undated, 2 pages.

Invibio, Biomaterials Solutions, "PEEK-Optima, Spiked Washers," Invibio Inc., Lancashire, United Kingdom, undated, 1 page.

Kambin; "Arthroscopic Microdiscectomy: Minimal Intervention in Spinal Surgery"; National Library of Medicine; 1991; pp. 67-100.

Kambin; "Percutaneous Posterolateral Discectomy"; Clincial Orthopaedics and Related Research, Section II; pp. 145-154.

Savitz; "Same-Day Microsurgical Arthroscopic Latera-Approach Laser-Assisted (SMALL) Fluoroscopic Discectomy"; Journal of Neurosurgery; Jun. 1994; pp. 1039-1045.

Schaffer et al.; "Percutaneous Posterolateral Lumbar Discectomy and Decompression with a 6.9 Millimeter Cannula"; Journal of Bone and Joint Surgery; 1991; pp. 822-831.

Sofamor Danek Video Systems Brochure.

Tangram Technology Ltd., "Polymer Data File: Polyether Ether Keotone-PEEK," Available at http://www.tangram.co.uk/TI-Polymer-PEEK.html, 2001, 5 pages.

Web pages, http://www.brainlab.com, Apr. 2, 2002; 5 pages.

Wiltse; "New Uses and Refinements of the Paraspinal Approach to the Lumbar Spine"; Spine; 1988; 13(6): pp. 696-706.

* cited by examiner

PEDICLE SEEKER AND RETRACTOR, AND METHODS OF USE

CROSS-REFERENCE TO RELATED APPLICATIONS

Priority is claimed from U.S. Provisional Patent Application No. 60/806,775 filed Jul. 8, 2006 entitled "Retractor and Guide," which is incorporated by reference in its entirety.

FIELD OF THE INVENTION

The present invention is generally directed to a novel pedicle seeker and retractor, and a method of using the combination of the pedicle seeker and retractor for a minimally invasive approach to setting surgical implants, and particularly for placing spinal pedicle screws.

BACKGROUND

Arthrodesis, also known as artificial ankylosis or syndesis, is a commonly used surgical procedure whereby two or more vertebrae are joined, fused or secured together to stabilize the spine. Arthrodesis may be done by itself, or in combination with other treatments such as decompression, in order to treat the pain that typically accompanies misalignment or instability of the vertebrae, such as spondylolisthesis, which can not be otherwise treated with pain medication, splints, or other normally-indicated treatments. Arthrodesis may also be done as a follow-up to decompression and debridement procedures that are performed to treat disorders such as spinal stenosis, herniated discs, spinal injuries, infection, tumors, and deformities.

Pedicle screw fixation has become an important part of stabilizing the spine to assist in arthrodesis. Pedicle screws do not fixate a vertebra or spinal segment themselves, but rather provide a means of gripping a vertebra and act as anchor points along a patient's spine that can then be connected with a rod or other stabilizing device. Traditionally, a significant amount of muscle dissection has been required to prepare for pedicle screw placement in the spine, which required longer surgical procedures as well as recovery times. Recently however, several alternative surgical approaches have been developed in an effort to minimize the amount of muscle dissection and unnecessary disturbance of paraspinous structures required in arthrodesis, while still accomplishing satisfactory placement of one or more pedicle screws and therefore fixation of the spine and the concomitant grafting necessary to achieve arthrodesis.

Once a surgical procedure opening the intermuscular planes to the spine has been performed, there are several options and methods that may be implemented to place a pedicle screw in the spine of a patient. For example, a retractor may be utilized by itself to locate and protect the pathway to a patient's spine for a conventional sequence of drilling and tapping, followed by placing a pedicle screw in the spine. While this approach is useful, it is typically more surgically invasive that other approaches. Alternatively, an awl may be used prior to surgery to palpate the bony surface and find the desired entry point to the patient's spine, with x-ray confirmation of position. Once the desired position is established, an incision is made through which the awl or seeker is tapped into the pedicle of the vertebral body, where the pedicle screw will be placed. However, this approach requires removal of the awl after tapping in order to place the pedicle screw in the bore created by the awl, which can result in a loss of position, with the entry point created for the screw being difficult to relocate.

Several devices, and combinations of devices, have been created to overcome the foregoing difficulties, such as those contemplated in U.S. Pat. No. 6,929,606 to Ritland and in U.S. Pat. No. 6,951,538, also to Ritland, both of which are incorporated by reference in their entirety. These devices utilize a combination of three separate instruments, a retractor, an awl, and an insert for the retractor through which the awl is placed and a bore created in the patient's spine, which is thereafter used to assist in the proper placement of a pedicle screw.

SUMMARY OF THE INVENTION

What is needed is a means of placing a surgical implant, and particularly a pedicle screw, at a specific location along the vertebra of a patient that can accurately pinpoint the desired location for placement, maintain the location of the specified point of placement until the implant has been properly placed, and that can guide the surgical implant from the exterior of the site down to the point of placement while using as few tools or devices as possible, thereby minimizing the amount of surgical time and personnel required to place an implant, and that can be used in at least one, and preferably several, minimally-invasive surgical approaches. The devices of the present invention accomplish these tasks. The present invention is generally directed to two devices, a novel pedicle seeker and a novel retractor, that can be used in combination to place a surgical implant, and particularly a pedicle screw, in the spine of a patient, as well as methods of using the combination of the pedicle seeker and retractor for a minimally invasive approach to setting surgical implants, and particularly for placing spinal pedicle screws. The pedicle seeker and retractor of the present invention, in combination, provides an advantage as to the intermuscular placement of surgical implants as compared to other known devices by using only two devices to place implants, as opposed to three or more, and by specifically eliminating the need to utilize an insert guide in order to properly place a surgical implant. Additionally, the present invention specifically lends itself to image guided applications, such as those contemplated in U.S. Pat. No. 6,929,606 to Ritland and in U.S. Pat. No. 6,951,538, also to Ritland. The characteristics of the pedicle seeker and retractor are described below with accompanying figures to illustrate the features.

One aspect of the present invention is directed to a surgical combination adapted for placement of a pedicle screw within a patient. A pedicle seeker having a tip, a distal end and a first flared portion, as well as a shaft, are sized and shaped to match the size and shape of a pedicle screw. A retractor, having a guide portion and a handle portion, is provided. The guide portion has a proximal channel, a distal channel and a second flared portion between the proximal channel and the distal channel. The handle portion is preferably angularly connected to a proximal end of the guide portion. The proximal channel, the distal channel and the second flared portion of the guide portion of the retractor are sized and shaped to approximate the size and shape of the pedicle seeker. In certain embodiments, the pedicle seeker itself comprises a handle. Preferably, the guide portion further comprises a groove located at its proximal end that extends at least partially along the proximal channel. The diameter of the distal end of the pedicle seeker is preferably at least about 3.0 mm and can range up to about 8.5 mm. The diameter of the shaft of the pedicle seeker is preferably from about 6.5 mm to about 8.5 mm.

Another aspect of the present invention is directed to a method for placing a spinal pedicle screw in a patient. Such method includes providing a pedicle seeker having a distal end that approximates the size, shape and/or length of a pedicle screw, with the pedicle seeker having a shaft of a sufficient length so as to extend beyond the face of a guide portion of a retractor. A surgeon uses the pedicle seeker to locate, typically by palpating the bony surface of a patient's spine, the proper place along a vertebrae to place an implant, such as a pedicle screw. Thus, one step of the preferred method is locating a desired position on a bony surface of a patient's spine with the pedicle seeker. A retractor is then placed and/or positioned in the surgical site such that a guide portion of the retractor is placed immediately adjacent to the pedicle seeker and is moved along the pedicle seeker into contact with the vertebrae. Thereafter, the pedicle seeker is removed from the surgical site, with the retractor remaining in a desired position. A pedicle screw is then moved down the length of the face of the retractor to a desired location for subsequent implantation of the pedicle screw in a patient's spine. Thus, one aspect of the present invention includes the step of guiding a desired implant, such as a pedicle screw, along the surface of a specially configured retractor, after the retractor has been properly positioned with a pedicle seeker device, and after the pedicle seeker device has been removed from the surgical site.

Additional advantages of the present invention will become readily apparent from the following discussion, particularly when taken together with the accompanying drawings.

It should be appreciated that the present Summary of the Invention admittedly does not discuss in detail each and every element and/or limitation of the present invention, with such elements, limitations, combinations, etc. being disclosed in the figures, the Detailed Description, Summary of the Invention, etc., without any limitation of the present invention being intended by an absence of its description in the Summary.

DETAILED DESCRIPTION OF THE INVENTION

To avoid traditional muscle dissection required in the placement of a surgical implant during arthrodesis, and to reduce the amount of surgical time and personnel required to place the implant, a pedicle seeker and retractor are provided. The pedicle seeker includes a distal end that approximates the size, shape and length of a surgical implant, and particularly a pedicle screw, and a shaft that is of sufficient length so as to extend beyond the face of the guide portion of the retractor of the present invention, allowing the pedicle seeker to be removed from the surgical site once the retractor has been placed. The pedicle seeker is first used to palpate the bony surface of the patient's spine in order to locate the proper place along a vertebra to place an implant. After the desired location has been located, the retractor is placed into the surgical site, the guide portion of the retractor being placed immediately behind the pedicle seeker and moved along the distal end of the pedicle seeker to the vertebra, and held in place in order to maintain the desired location for placement of the surgical implant, and the seeker is removed. The retractor is of appropriate length to provide access from the skin surface to the dorsal aspect of the vertebra over the pedicle. The retractor includes surficial features that approximate the distal end of the pedicle seeker, and therefore the surgical implant, to allow the surgical implant to be moved down the length of the face of the retractor to the desired location for implantation. The retractor therefore also provides a guide for the desired implant to be placed from the skin surface to the desired entry point and is configured to retract as the implant is advanced into position, allowing the implant to be placed directly into the desired location, with the implant being positioned at the protected entry point. As can be appreciated, the use of two devices for accurate, protected placement of a surgical implant is advantageous as compared to the use of three or more devices to accomplish the same task, as the amount of time and surgical personnel required to place the implant will both be reduced. The pedicle seeker and retractor of the present invention thus allow for accurate, protected placement of a surgical implant without the use of a retractor insert, or similar article.

Figure 1A:
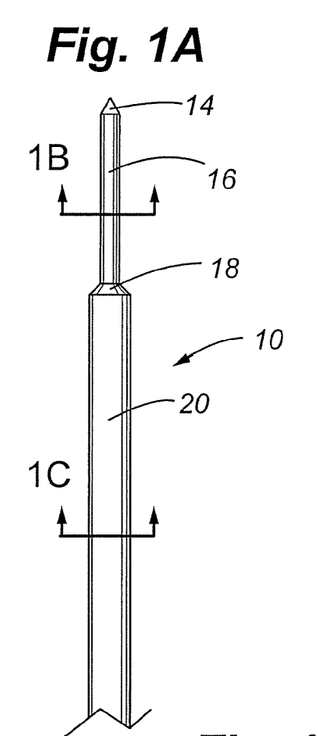
FIG. 1A is a plan view of one embodiment of a pedicle seeker according to at least some aspects of the present invention.
Figure 1B:
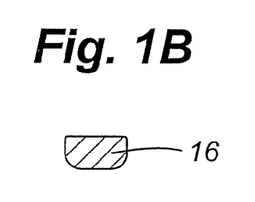
FIG. 1B is a horizontal cross-sectional view of the distal end of the pedicle seeker shown in FIG. 1, taken along line 1B of FIG. 1.
Figure 1C:
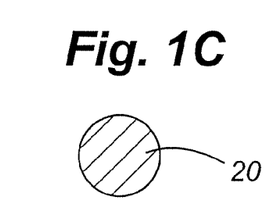
FIG. 1C is a horizontal cross-sectional view of the shaft of the pedicle seeker shown in FIG. 1, taken along line 1C of FIG. 1.

Referring now to FIGS. 1A, 1B and 1C, a pedicle seeker 10 according to at least some embodiments of the present invention is presented. The pedicle seeker 10 minimally includes a tip 14, a distal end 16, a flared portion 18 and a shaft 20. In some embodiments, the pedicle seeker 10 may include a handle portion at the end of the shaft (not shown), to facilitate use. In operation, the pedicle seeker 10 is utilized in a manner similar to a probe, whereby the tip 14 is used to palpate the bony processes of one or more vertebrae along the spine in order to locate the proper place along the dorsal aspect of one or more vertebrae to place a surgical implant. It is preferable that the pedicle seeker 10, and all of its respective structural parts including without limitation the tip 14, not be sharp or configured so as to be able to cause any inadvertent damage or trauma to the patient during probing. In an alternate embodiment, however, the pedicle seeker 10 may include threading on at least a portion of the distal end 16 as well as on the tip 14, and the tip 14 may be sufficiently sharp, so as to allow the pedicle seeker 10 to be used as a tap or bore tool after the proper location for the implant has been located and secured by the retractor of the present invention.

In the presently preferred embodiment, the structures of the pedicle seeker 10 are sized and shaped to approximate, and even more preferably match, the size and shape of the desired surgical implant so that the pedicle seeker 10 can be used to accurately measure the surgical site to determine if it is of sufficient size to be able to receive the desired implant. In this manner, if a proposed surgical size appears to be too small to accommodate the structures of the pedicle seeker 10, then it is also likely to be too small to accommodate the desired implant. By way of example, and without wishing to be limited to any structure or implant, presume that the surgical implant of interest is a pedicle screw. In order for the pedicle seeker 10 to be sized to approximate, and preferably match, the pedicle screw, the tip 14 is sized, in length, angle and width, to match the tip of the desired pedicle screw, the distal end 16 of sized, in length and width, to match the threaded shaft of the pedicle screw, and at least a portion of the shaft 20 is sized in width to match the head of the pedicle screw. Additionally, the flared portion 18 between the distal end 16 and the shaft 20 of the pedicle seeker 10 is sized, in length, angle and width, to match the flared portion on a pedicle screw located between its threaded shaft and the screw head (see also FIG. 3). It is worthy to note that, in the foregoing example, the tip 14 in the preferred embodiment would not include threading as the tip of the pedicle screw would, but would rather merely match the size of the screw tip without including any structures that may cause inadvertent damage to the patient during use. It is also preferable that the distal end 16 not be threaded in the same manner as the threaded portion of a pedicle screw, so as to allow the pedicle seeker 10 to freely move from one location to another along a patient's spine without the danger of damaging the patient's spinal musculature through accidental contact with the threading. By having the pedicle seeker 10 sized so as to approximate, and preferably to match, the size of the implant of interest, the surgeon can utilize the pedicle seeker 10 to accurately determine the surgical procedure that will be necessary to place the implant, and will avoid making incisions that are unnecessarily large for the size of the implant to be placed in the vertebra (e). It is therefore an object of the present invention that the pedicle seeker 10 be sufficiently scalable so that it may approximate the size, shape and length of any number of desired surgical implants irrespective of their size. While not wishing to be bound to any structures or implants, the surgical implants that may be used with the present invention include, without limitation, polyaxial pedicle screws, monoaxial pedicle screws, bone screws, dental implants, bio active drug delivery devices and similar implants requiring surgical implantation where minimally-invasive procedures are desired.

As shown in FIG. 1B, in some embodiments the distal end 16 of the pedicle seeker 10 may have a cross section that is not substantially circular in shape, but is flattened on at least one side. In these embodiments, the distal end 16 may be flattened on one or two sides, thereby reducing its profile and thus its impact on the patient when in use. Notwithstanding the flattened aspects depicted in these embodiments, the total width of the non-flattened portions of the distal end 16 are still preferably sized to approximate the desired surgical implant, thereby still allowing the surgeon to accurately determine the surgical procedures that will be necessary to place the implant in the patient, while the flattened edges facilitate removal of the pedicle seeker 10 from the site via the retractor of the present invention. In the presently preferred embodiment, the cross-sectional diameter of the distal end 16 is circular and the size of its diameter preferably ranges from about 2.0 mm to about 9.0 mm, even more preferably from about 3.0 mm to 8.5 mm, and is even more preferably approximately 3.5 mm in diameter. As can be seen in FIG. 1C, the shaft 20 of the pedicle seeker 10 is substantially cylindrical, and therefore circular in cross-section. In the presently preferred embodiment, the size of the diameter of the shaft 20 of the pedicle seeker 10 preferably ranges from about 5.0 mm to about 10.0 mm, even more preferably from about 6.5 mm to 8.5 mm, and is even more preferably approximately 7.5 mm in diameter. It is also preferable that the shaft 20 be longer than the guide portion of the retractor of the present invention (described below), in order to allow the surgeon to maintain control of the pedicle seeker 10 while placing the retractor of the present invention at the surgical site and also allowing the pedicle seeker to be easily removed from the surgical site once the retractor has been properly placed.

Figures 2A, 2B, 3:
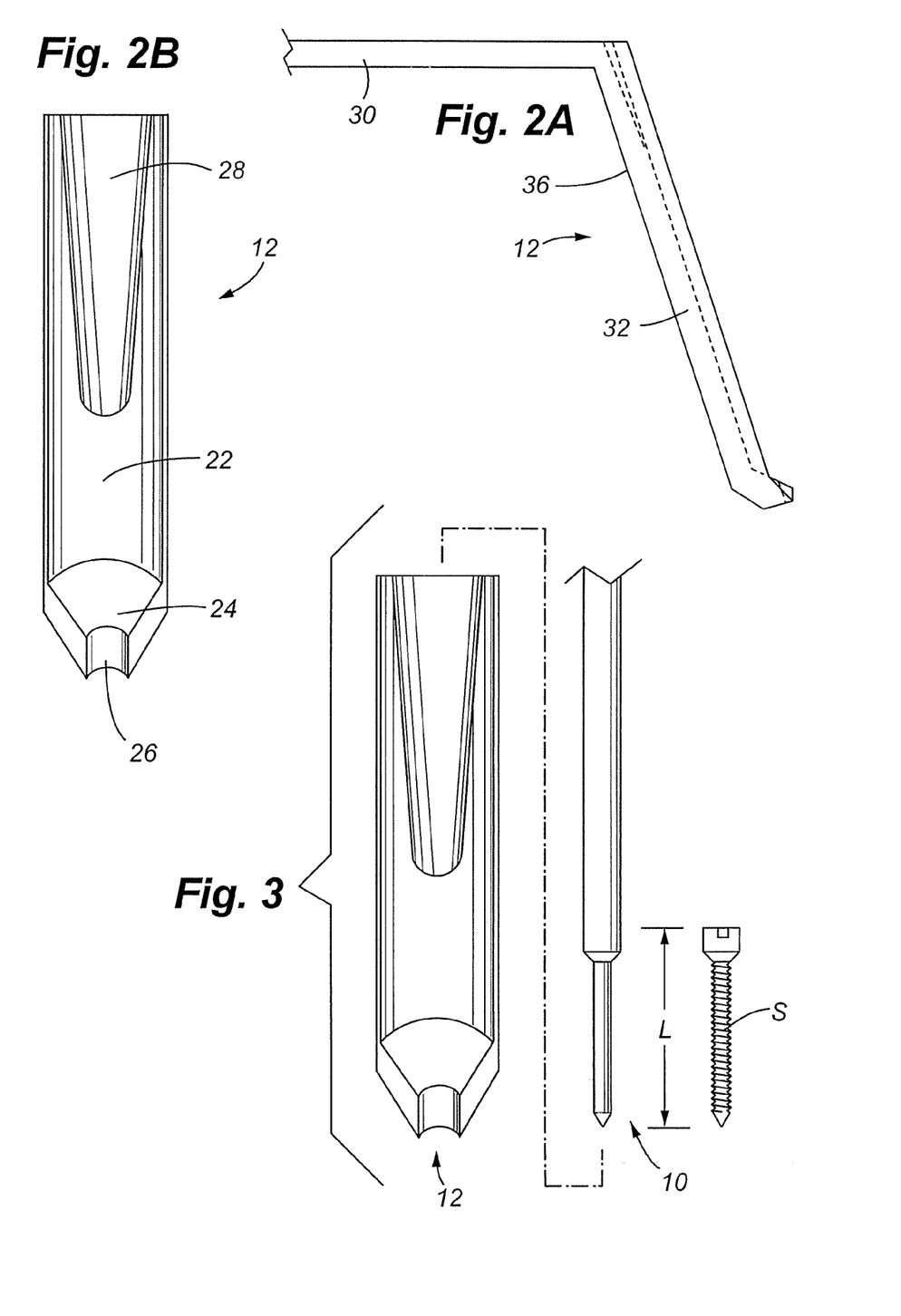
FIG. 2A is a side plan view of one embodiment of a retractor according to at least some embodiments of the present invention.
FIG. 2B is a front elevation view of one embodiment of a retractor according to at least some embodiments of the present invention.
FIG. 3 is a front elevation view of one embodiment of a pedicle seeker, one embodiment of a retractor, and a pedicle screw according to at least some aspects of the present invention.

Referring now to FIGS. 2A and 2B, a retractor 12 according to at least some embodiments of the present invention is presented. The retractor 12 minimally includes a handle portion 30 and a guide portion 32, the guide portion including a proximal channel 22, a distal channel 26, and a flared portion 24 between the proximal channel 22 and distal channel 26. The guide portion 32 may also optionally include a groove 28 at its proximal end to facilitate removal of the pedicle seeker 10 and/or placement of an implant, as appropriate. The handle portion 30 is attached to the proximal end of the guide portion 32 and may be of various configurations to allow access to the surgical site while providing a means of gripping the retractor 12, so that sufficient leverage may be applied to the retractor 12 in order to maintain its desired orientation and location against the lateral aspects the paraspinous musculature at the surgical site. The handle portion 30 may be oriented at any angle of between about 90 and about 180 degrees from the guide portion 32, depending upon the surgical procedure necessary. In some embodiments, the guide portion 32 is detachably connected to the handle portion 30 thereby allowing for adjustment of the angle between the handle portion 30 and the guide portion 32 during use, and also allowing the guide portion 32 to be used on its own, without the handle portion 30, to place an implant. This detachable connection may be accomplished by any one or more of many standard means by which two mechanical structures may be operably connected together, such as screws, bolts, a clamp, a snap-fit assembly, a push-on/turn-on self-locking fastener, a press fit, rivets, a quick connect coupling, or similar means, thereby allowing various configurations of guide portions 32 to be interchangeably connected to the handle portion 30. As a result, various guide portions 32 can be produced having a variety of depths and groove 28 configurations, and the surgeon can attach the desired guide portion 32 deemed appropriate for the given surgical conditions at a desired angle.

It is also preferable for the guide portion 32 to be of an appropriate length to provide access from the skin surface to the dorsal aspect of the vertebra over the pedicle and to maintain the amount of muscle retraction necessary for placement of the implant. In operation, the retractor 12 is used by the surgeon after the proper location for placement of the implant has been determined by use of the pedicle seeker 10. Using the handle portion 30 of the retractor 10, or using the guide portion 32 alone if the retractor 10 is being used without the handle portion 30 attached to it, the guide portion 32 is moved into the surgical site behind the pedicle seeker 10, retracting tissue away from the site pinpointed by the pedicle seeker 10, in order to maintain access to the interior of the surgical site at the desired location for placement of the implant, as described in greater detail below. The guide portion 32 of the retractor 12 is preferably open at its face to facilitate easy removal of the pedicle seeker 10 from the surgical site after the retractor 12 is placed, and to facilitate proper placement of the desired implant. In the presently preferred embodiment, the guide portion 32 is half-cylinder or U-like in shape and is sized to approximate the size and shape of the structural features of the pedicle seeker 10. More specifically, the rear surface 36 of the guide portion 32 is convex when viewing the retractor 12 from the rear or side (FIG. 2A), thereby creating the half-cylinder of U-like shape of the guide portion 32. Additionally, the guide portion 32 is straight-sided from the point of attachment to the handle portion 30 to approximately the flared portion 24 in order to retract as little tissue as possible and thereby maintain the usefulness of the present invention in minimally-invasive surgical procedures. In an alternate embodiment, the guide portion 32 may have one or more flared sides, which would expand outward from the flared portion 24 to the point of attachment of the handle portion 30 and thereby produce an angled look to one or both sides of the guide portion 32 when viewed from the front, to protect a larger diameter for entry such as might be needed by an implant that is substantially conical in shape or that has features making one side larger than the other.

The U-shaped front of the guide portion 32 includes a wide hollow region or proximal channel 22 extending from the proximal end of the guide portion 32 to the top, or most proximal end, of the flared portion 24. In the presently preferred embodiment, the proximal channel 22 approximates the size of the shaft 20 of the pedicle seeker 10, and therefore that portion of the desired implant that is complimentary to at least a portion of the shaft 20, and may be used as a guide to smoothly remove the pedicle seeker 10 from the surgical site and to move the desired implant, and particularly a pedicle screw, down to the interior-most portion of the surgical site by inserting the implant into the proximal channel 22. The guide portion 32 also includes a narrow hollow region or distal channel 26 extending from the bottom of the flared portion 24 to the distal most portion of the guide portion 32, and a flared portion 24 between the proximal channel 22 and the distal channel 26. The flared portion 24 is preferably sized to approximate the flared portion 18 of the pedicle seeker 10, and therefore that portion of the desired implant that is complimentary to the flared portion 18, and the distal channel 26 is preferably sized to approximate the size and shape of the distal portion 16 of the pedicle seeker 10, and therefore that portion of the desired implant that is complimentary to the distal portion 16. It is important to note that, in the presently preferred embodiment, the sizing of each feature of the guide portion 32 approximates the sizes of those corresponding features of the pedicle seeker 10 and of the implant that is to be placed in the vertebra of the patient, but does not match that sizing exactly. It is therefore preferable for the guide portion 32 to be sized so as to be larger than the corresponding portions of the pedicle seeker 10 and desired implant, by a minimal amount (e.g. less than 1.0 mm) so as to allow the retractor 12 to cooperatively fit with the pedicle seeker 10 in operation while not making the size and shape of the retractor 12 too small to ensure proper operation, and to allow the corresponding implant, and particularly a corresponding pedicle screw, to move easily within the guide portion 32 without getting stuck or lodged in any manner.

In some embodiments, the guide portion 32 of the retractor 12 includes a groove 28 located within the proximal channel 22 that extends from the proximal end of the guide portion 32 downward toward the flared portion 24, at least partially into the proximal channel 22. The groove 28 is a second channel-like feature optionally formed in the proximal channel 22 that serves as an additional guide plane for the shaft 20 of the pedicle seeker 10, and therefore for a corresponding structure in a desired surgical implant, and/or for other surgical instruments that may be necessary for the procedure being performed. The groove 28 may be formed in only a portion of the proximal channel 22, such as the upper half or upper one-third of the proximal channel 22 and may be as wide as the proximal channel 22 or narrower. In the preferred embodiment when a groove 28 is present, that portion of the groove 28 located along the proximal portion of the guide portion 32 is as wide as the proximal channel 22 and thereafter the groove 28 tapers from the proximal end of the guide portion 32 to its desired point of termination along the proximal channel 22 to a width that is substantially narrower than the proximal channel 22. Additionally, the groove 28 may be of a variety of depths set into the interior surface of the proximal channel 22. For example, the groove 28 may be relatively shallow near the handle portion 30, such that it cradles only a portion of the shaft 20 of the pedicle seeker and/or a complimentary portion of the desired implant, or it may relatively deep near the handle portion 30 such that it cradles all, or nearly all, of the circumference of the shaft 20 of the pedicle seeker and/or a complimentary portion of the desired implant.

Referring now to FIG. 3, a retractor 12 and pedicle seeker 12 according to at least some embodiments of the present invention are shown in plan view with a pedicle screw S, which is a preferred implant for use with the present invention. In the depicted preferred embodiment, the distal portion of the pedicle seeker 10 is sized to approximate, and even more preferably to match, the size, shape and length L of the screw S. More specifically, the tip 14 of the pedicle seeker 10 is sized to match the tip of the screw S, the distal end 16 of the pedicle seeker 10 is sized to match the threaded portion of the screw S, the flared portion 18 of the pedicle seeker 10 is sized to match the flare of the screw S, and a portion of the shaft 20 of the pedicle seeker 10 is sized to match the head of the pedicle screw S. As can be appreciated, the pedicle seeker 10 in this embodiment can be used as an accurate measure for the size and shape of the screw S to be placed in the patient's spine. In this regard, in the event that a surgeon has several pedicle screws S of varying sizes to place along a patient's spine, the surgeon may implement any number of pedicle seekers, each sized as described above to match the varying screws S, to locate the proper sites along the vertebrae for placement of the screws in the most minimally-invasive manner possible. Additionally, the broken line depicted in FIG. 3 shows the manner in which certain embodiments of the pedicle seeker 10 may be placed into certain embodiments of the retractor 12 during use, as well as the relationship of the structural features of those embodiments of the pedicle seeker 10, and therefore the structural features of the screw S, to the structural features of those embodiments of the retractor 12.

Figure 4A:
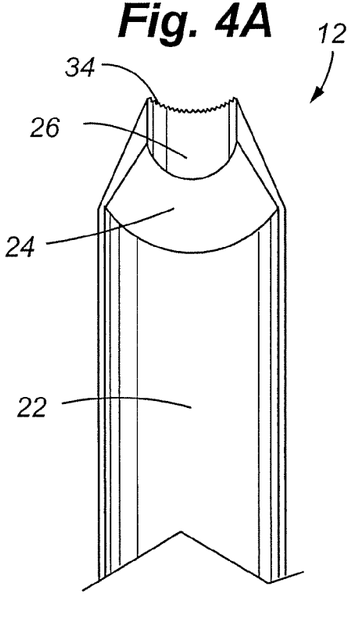
FIG. 4A is a front elevation view of an embodiment of the distal portion of a retractor of according to at least some embodiments of the present invention.
Figure 4B:
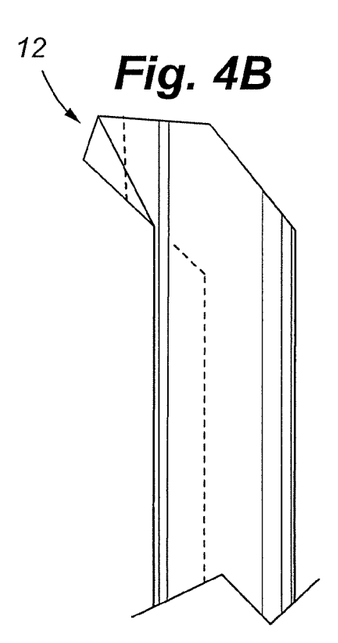
FIG. 4B is a side plan view of an embodiment of the distal portion of a retractor of according to at least some embodiments of the present invention.

Referring now to FIGS. 4A and 4B, two plan views of the distal end of a retractor 12 according to at least some embodiments of the present invention are shown. In the depicted embodiments, the rear surface 36 of the flared portion 24 of the guide portion 32 and the distal channel 26 of the retractor 12 are convex or when viewed from the side or the back (FIG. 4B) and may taper or angle toward the most distal portion of the distal channel 26 to direct tissue away from the shaft 20 of the pedicle seeker 10 during placement of the retractor 12 to help avoid interposition of tissues between the shaft 20 and the retractor 12. This taper or angle facilitates easy placement of the retractor 12 at the surgical site, which has been previously pinpointed by the tip 14 of the pedicle seeker 10, with minimal muscle separation, thus helping to displace soft tissues while placing the retractor 12 and minimizing the tendency of the retractor 12 to catch on soft tissue during entry into the surgical site. In that regard, the proximal channel 22, distal channel 26, and flared portion 24 of the retractor 12 are all appropriately sized to the diameter of the shaft 20, distal end 16 and flared portion 18 of the pedicle seeker, respectively, to engage these structures and slide down the pedicle seeker 10 into the surgical incision with minimal tissue interference. When the guide portion 32 of the retractor 12 is properly placed at the surgical site, the distal surface of the distal channel 26 appears as a cutout, preferably as a semi-circular or curved cutout, surrounding the desired point of implantation of the surgical implant, and is preferably sized at its distal surface to allow use of a tap and subsequent placement of the appropriate implant, and particularly a pedicle screw. As shown in FIG. 4A, the distal surface of the distal channel 26 may be textured and obliquely cut to help maintain position of the retractor against a patient's vertebra. Preferably, there are a plurality of projections 34 creating a textured surface along the distal surface of the distal channel 26 of the retractor 12 to help maintain position against the bone once the retractor 12 is placed, and to avoid displacement while working through the retractor 12. In this embodiment, one or more projections 34 may be provided around the end-most portion of the distal channel 26 to aid in maintaining the position of the retractor 12 during use by stabilizing retractor 12 against the bony surface of the vertebrae.

All components of the invention and its various embodiments and alternatives described herein are manufactured of a material appropriate for surgical use. For example, the components can be made of surgical grade and/or quality stainless steel. However, it is to be understood that other types of materials may also be used, such as titanium or ceramics. Alternatively, it is yet another aspect of the present invention that the retractor 10 may be manufactured of surgical quality plastics or other disposable materials. This manufacturing aspect allows for relatively inexpensive production of a surgically sterile retractor 10 that can be disposed after each use. This type of manufacturing would allow several varying embodiments of the retractor 12 to be made quickly and easily, thereby allowing a surgeon to pick one or more retractor 10 configurations having different guide portion 32 arrangements to match the surgical procedure(s) to be performed. Alternatively, disposable guide portions 32 can be produced for temporary attachment to a reusable handle portion 30.

Figure 5A:
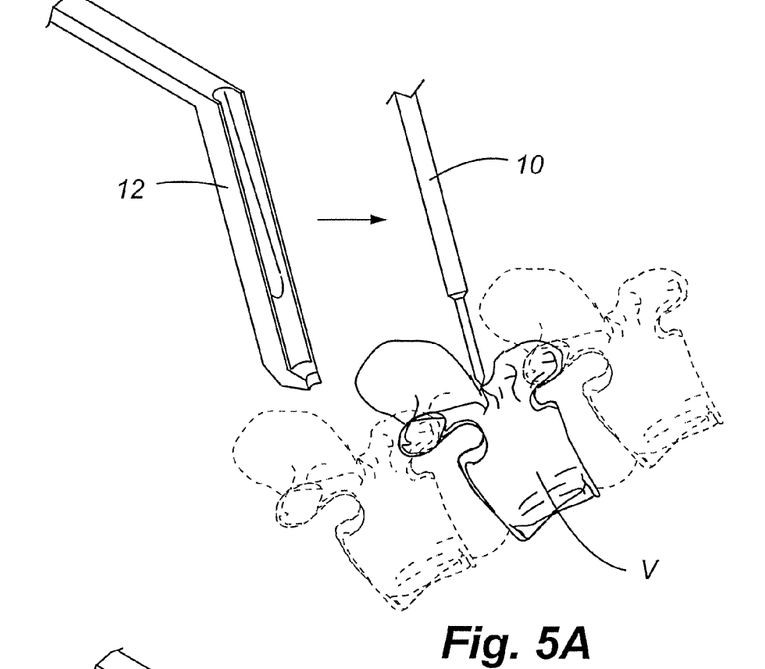
FIG. 5A is a plan view of a pedicle seeker according to at least some aspects of the present invention, shown in simulated application with a human vertebra.
Figure 5B:
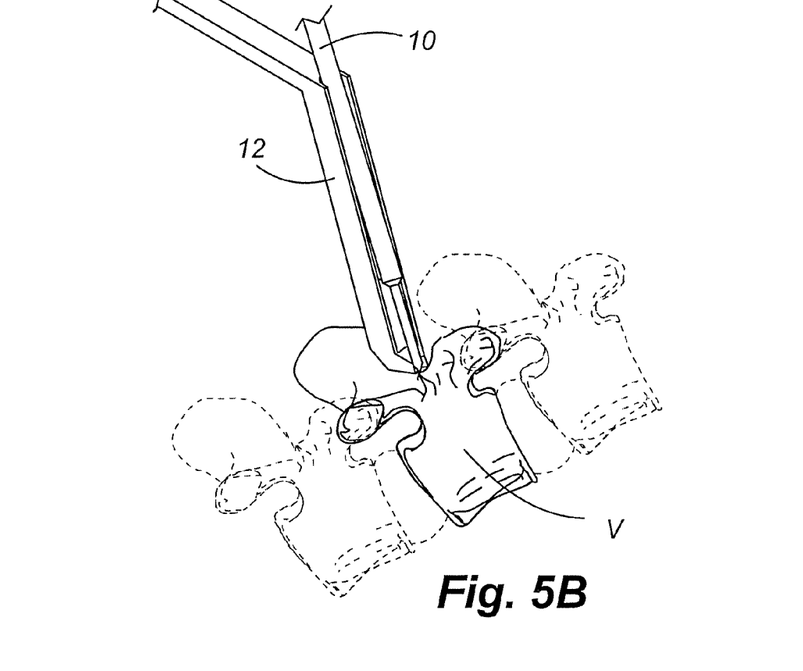
FIG. 5B is a plan view of a pedicle seeker and a retractor according to at least some aspects of the present invention, shown in simulated application with a human vertebra.

Referring now to FIGS. 5A, 5B, 5C and 5D, a method of using a combination of the pedicle seeker 10 and retractor 12 of the present invention to place the desired implant, which is preferably a pedicle screw S, into the vertebra V of a patient during arthrodesis is described. Typically, an incision is made in the patient's skin and muscle over the vertebra V of interest and subperioseal dissection of the musculature from the spinous processes is performed on both sides, to the level of the transverse processes in the spine. Subsequently, the pedicle seeker 10 is utilized by the surgeon to palpate the bony regions of the vertebra V of interest, to determine the proper location along the patient's spine for placement of the pedicle screw S. More specifically, the tip 14 of the pedicle seeker 10 is probed along the surface of the vertebra V until the proper location for screw S placement is identified. The tip 14 of the present invention is preferably not sharp enough to penetrate the musculature of the patient and, in some embodiments, may be blunted or rounded so as to prevent inadvertent injury or trauma during use. In FIG. 5A, the pedicle seeker 10 is shown in one possible relationship with the human spine after the surgeon has used it to locate the desired point on the vertebra V for placement of the pedicle screw S. Once the proper location for placement of the screw S has been located, the pedicle seeker 10 is held in place by the surgeon, while the retractor 12 is moved in behind the pedicle seeker 10 as shown in FIGS. 5A and 5B as described below.

Figure 5C:
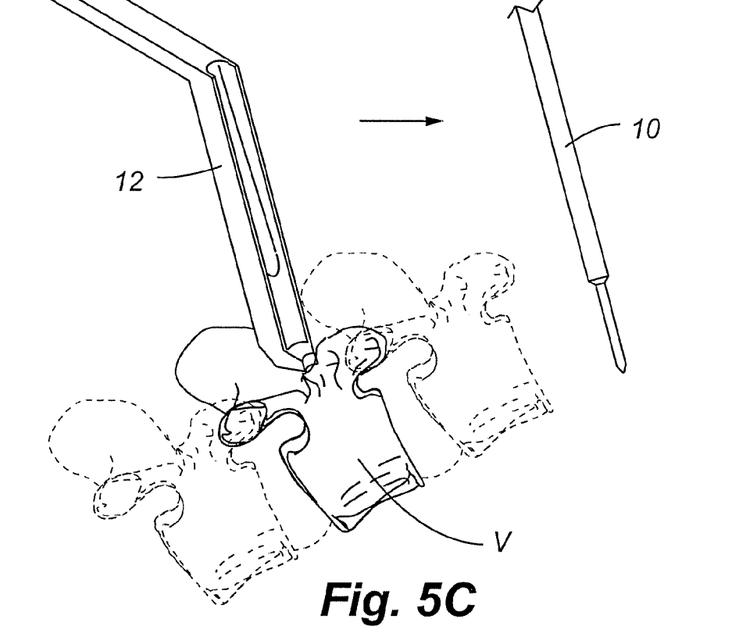
FIG. 5C is a plan view of a retractor according to at least some aspects of the present invention, shown in simulated application with a human vertebra, wherein the pedicle seeker shown in FIG. 5A has been removed.

The guide portion 32 of the retractor 12 is inserted through the exterior portion of the incision and slid down the pedicle seeker 10 to the location marked by the tip 14 of the pedicle seeker 10 in order to create and maintain access to the targeted vertebra V (FIG. 5B). The guide portion 32 may be inserted via use of the handle portion 30, or may be inserted directly without use of the handle portion 30 as determined by the surgeon. Once properly placed, the retractor 12 may be secured with a surgical arm to maintain its position along the vertebra V. Once sufficient access to the targeted vertebra V has been established by the retractor 12, and the distal surface of the distal channel 26 has made contact with the vertebra V so that the projections 34 located along the end-most portion of the distal channel 26, provided they are present in the embodiment in use by the surgeon, also make contact with the vertebra V and stabilize the retractor 12 against the bony surface of the vertebrae V, the pedicle seeker 10 may be removed from the surgical site (FIG. 5C). At this point, the surgeon may opt to utilize a tool called a tap in order to tap a thread in the vertebra V for subsequent insertion of the screw S. This step is not required in all surgical applications, however, and thus may not be performed. A tap may be inserted down the guide portion 32 of the retractor 12 to the site of screw S insertion via the proximal channel 22, flared portion 24 and distal channel 26 much in the same manner as the pedicle seeker 10. In this regard, if the retractor 12 chosen for use by the surgeon includes a groove 28, the tap may be initially placed into the proximal channel 22 via the groove 28, which will serve as an additional guide plane for the tap as it is slid along the guide portion 32 toward the surgical site. The tap may be sized in diameter so as to restrict its passage beyond a specified length through the guide portion 32. Specifically, the tap may contain handle portion that is too large in diameter to fit into the flared region 24 of the guide portion 32, thereby preventing passage of the tap 33 beyond the point where the tap handle contacts the flared region 24 and preventing the tap from boring too far into the vertebra V. Once at the site, the tap is used to create an appropriate bore in the vertebra V for receipt of the pedicle screw S. In an alternative embodiment, the tip 14 of the pedicle seeker 10 may be configured in a similar manner as a tap, thereby allowing the surgeon to utilize the pedicle seeker 10 as a tap, thus obviating the need for a separate tool.

Figure 5D:
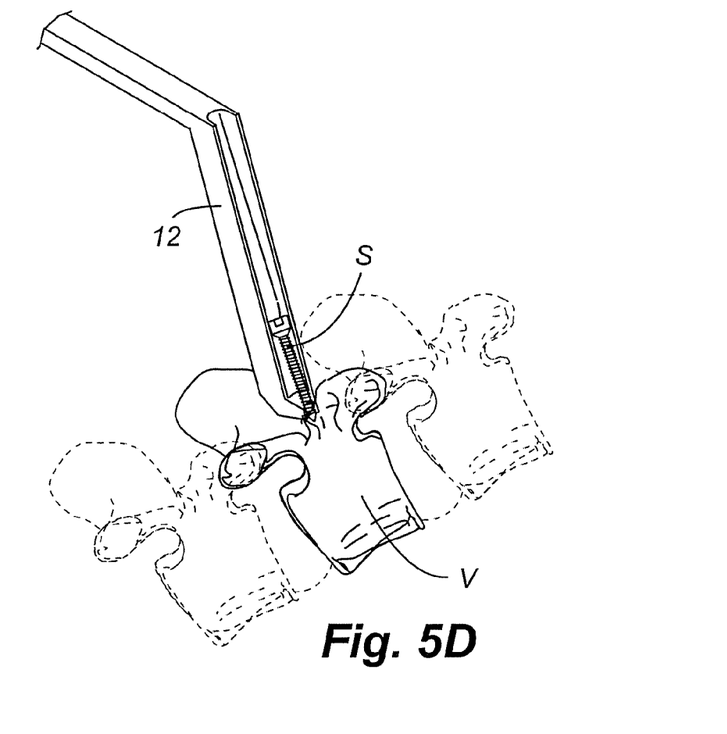
FIG. 5D is a plan view of a retractor and a pedicle screw according to at least some aspects of the present invention, shown in simulated application with a human vertebra.

Once the tapping operation is complete, provided it was performed, the tap may be removed from the retractor 12 in the same manner as the pedicle seeker 10. The retractor 12 remains in place at the surgical site and is then used to guide a pedicle screw S down from the exterior of the site to the proper location along the vertebra V, as shown in FIG. 5D. The retractor 12, and particularly the proximal channel 22, the groove 28 if any, the flared region 24 and the distal channel 26, provide for proper alignment of the screw S as it is advanced into the vertebra V. More specifically, as described herein, the proximal channel 22, the flared region 24 and the distal channel 26, are all sized and shaped to accommodate the specific screw S to be utilized so that screw S may be properly aligned with the desired surgical site and/or the bore created by the tap. Once the screw S is in place at the vertebra V, a proper tool, such as a medical screwdriver, is then utilized to finish installation of screw S by advancing the screw S into the vertebra V. Placement of the screw S is thereafter accomplished with the retractor 12 being allowed to shift out of guide position with the final seating of the screw S, or to be removed from the site entirely by the surgeon, as the screw S is advanced toward the vertebra V and the head of the screw S is seated to the vertebra V.

The present invention, in various embodiments, includes components, methods, processes, systems and/or apparatuses substantially as depicted and described herein, including various embodiments, subcombinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, e.g., for improving performance, achieving ease and/or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover though the description of the invention has included descriptions of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A surgical combination adapted for placement of a pedicle screw having a size and shape within a patient, comprising:
   a pedicle seeker having a tip, a distal end, a first flared portion and a shaft; and
   a retractor having a guide portion and a handle portion, said guide portion having a proximal channel, a distal channel, and a second flared portion between said proximal channel and said distal channel and said handle portion being angularly connected to a proximal end of said guide portion;
   wherein the retractor is adapted to be placed in slidable engagement with the pedicle seeker after the pedicle seeker is pre-positioned within the patient;
   wherein said tip, said distal end, said first flared portion and said shaft of said pedicle seeker are sized and shaped to match the size and shape of said pedicle screw; and
   wherein said proximal channel, said distal channel and said second flared portion of said guide portion of said retractor are sized and shaped to accommodate the size and shape of said pedicle seeker.

2. The surgical combination of claim 1, wherein said pedicle seeker further comprises a handle.

3. The surgical combination of claim 1, wherein said guide portion further comprises a groove located at its proximal end and extending at least partially along said proximal channel.

4. The surgical combination of claim 1, wherein the diameter of said distal end of said pedicle seeker is from about 3.0 millimeters to about 8.5 millimeters.

5. The surgical combination of claim 1, wherein the diameter of said shaft of said pedicle seeker is from about 6.5 millimeters to about 8.5 millimeters.

6. A surgical combination adapted for placement of a pedicle screw having a size and length within a patient, comprising:
   a pedicle seeker having a size and shape, including a tip, a distal end with a diameter of about 3.5 millimeters, a first flared portion, a shaft having a diameter of about 7.5 millimeters and a handle;
   a retractor having a guide portion and a handle portion, said guide portion having a proximal channel extending longitudinally along at least a first portion of a face of said guide portion, a distal channel extending longitudinally along at least a second portion of the face of said guide portion, a second flared portion located between said proximal channel and said distal channel and a groove located at the proximal end of said guide portion and extending at least partially along said proximal channel, and said handle portion including means for angular connection to a proximal end of said guide portion;
   wherein the retractor is adapted to be placed in slidable engagement with the pedicle seeker after the pedicle seeker is pre-positioned within the patient;
   wherein said tip, said distal end, said first flared portion and at least a portion of said shaft of said pedicle seeker are sized to match the size and length of said pedicle screw; and
   wherein said proximal channel, said distal channel and said second flared portion of said guide portion of said retractor are sized to accommodate the size and shape of said pedicle seeker.

7. A method for placing a spinal pedicle screw in a desired location of a patient's spine, comprising:
   providing a pedicle seeker having a tip, a distal end, a first flared portion and a shaft;
   providing a retractor having a guide portion and a handle portion, said retractor having a channel adapted for receiving the pedicle seeker and configured so that the retractor is able to slidably engage with the pedicle seeker so that the retractor is positioned into contact with a desired bony position on a patient's spine;
   directing said pedicle seeker to a desired location on a bony process of a patient's spine;
   directing said retractor along said pedicle seeker until said retractor is contacting said patient's bony process adjacent said pedicle seeker;
   removing said pedicle seeker from the desired location while retaining said retractor in the desired position;
   directing a pedicle screw along said guide portion of said retractor; and
   implanting said pedicle screw into said bony process of the patient.

* * * * *